United States Patent
Tan et al.

(10) Patent No.: US 10,336,745 B2
(45) Date of Patent: Jul. 2, 2019

(54) PIPERAZINE-CONTAINING TWO-PHOTON ABSORBING COMPOUNDS

(71) Applicant: The United States of America, as represented by the Secretary of the Air Force, Washington, DC (US)

(72) Inventors: Loon-Seng Tan, Centerville, OH (US); Zhenning Yu, Beavercreek, OH (US)

(73) Assignee: The United States of America as represented by the Secretery of the Air Force, Washington, DC (US)

( * ) Notice: Subject to any disclaimer, the term of this patent is extended or adjusted under 35 U.S.C. 154(b) by 0 days.

(21) Appl. No.: 15/910,341

(22) Filed: Mar. 2, 2018

(65) Prior Publication Data
US 2018/0273524 A1    Sep. 27, 2018

Related U.S. Application Data

(60) Provisional application No. 62/474,457, filed on Mar. 21, 2017.

(51) Int. Cl.
  C07D 417/14    (2006.01)
  C07D 277/66    (2006.01)

(52) U.S. Cl.
  CPC ......... *C07D 417/14* (2013.01); *C07D 277/66* (2013.01)

(58) Field of Classification Search
  CPC .................................. C07D 417/14
  USPC ...................................... 544/368
  See application file for complete search history.

(56) References Cited

U.S. PATENT DOCUMENTS

| 5,770,737 | A  | 6/1998  | Reinhardt et al. |
| 6,100,405 | A  | 8/2000  | Reinhardt et al. |
| 6,300,793 | B1 | 10/2001 | Ting et al. |
| 6,555,682 | B1 | 4/2003  | Kannan et al. |
| 6,730,793 | B1 | 5/2004  | Kannan et al. |
| 6,867,304 | B1 | 3/2005  | Tan et al. |
| 7,067,674 | B1 | 6/2006  | Kannan et al. |
| 7,319,151 | B1 | 1/2008  | Tan et al. |
| 8,153,812 | B1 | 4/2012  | Tan et al. |
| 8,471,035 | B1 | 6/2013  | Tan et al. |
| 8,580,958 | B1 | 11/2013 | Tan et al. |
| 8,674,057 | B1 | 3/2014  | Tan et al. |
| 8,735,528 | B1 | 5/2014  | Tan et al. |
| 8,895,730 | B2 | 11/2014 | Tan et al. |
| 9,024,037 | B1 | 5/2015  | Tan et al. |

OTHER PUBLICATIONS

I. Laios et la., "Effects of (R,S)/(S,R)-4,5-bis(2-chloro-4-hydroxyphenyl)-2-imidazolines and (R,S)/(S,R)-2,3-bis(2-chloro-4-hydroxyphenyl)piperazines on estrogen receptor alpha level and transcriptional activity in MCF-7 cells," Biochem. Pharamcol., vol. 74 (2007) 1029-1038.

N. Duguet et al., "Chiral relay in NHC-mediated asymmetric beta-lactam synthesis II: asymmetry from NHCs derived from acyclic 1,2-diamines," Tetrahedron: Asymmetry, vol. 21 (2010) 601-616.

O. Sereda et al., "Enantiopure imidazolinium-dithiocarboxylates as highly selective novel organocatalysts," Chem. Commun. (2009) 1040-1042.

Y. Matsumoto et al., "C2 symmetric chiral NHC ligand for asymmetric quaternary carbon constructing copper-conjugate addition of Grignard reagents to 3-substituted cyclohexenones," J. Org. Chem., vol. 73 (2008) 4578-4581.

A. R. Morales et al., "Amine-reactive fluorene probes: synthesis, optical characterization, bioconjugation, and two-photon fluorescence imaging," Bioconjugate Chem., vol. 19 (2008) 2559-2587.

J. Daniel et al., "pKa tuning in quadruplar-type two-photon ratiometric fluorescent membrane probes," Chem Commun, vol. 51 (2015) 15245-15248.

F. Jin et al., "Enhanced two-photon excited fluorescence of mercury complexes with a conjugated ligand: effect of the central metal ion," J. Lumines., vol. 172 (2016) 264-269.

X. Zhu et al., "A two-photon off-on fluorescence probe for imaging thiols in live cells and tissues," Photochem. Photobiol. Sci., vol. 15 (2016) 412-419.

D. J. Stewart et al., "The fluorescence of a chelating two-photon-absorbing dye is enhanced with the addition of transition metal ions but quenched in the presence of acid," Proc. SPIE, vol. 9939 (2016) 993904, 10 pages total.

(Continued)

*Primary Examiner* — Kahsay Habte
(74) *Attorney, Agent, or Firm* — AFMCLO/JAZ; Chastity Whitaker

(57) ABSTRACT

A two-photon absorbing (TPA) compound is provided along with a method of making same. The TPA compound has a general structural formula:

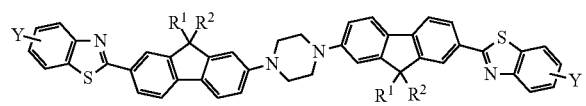

where $R^1$ and $R^2$ are independently selected from the group consisting of linear or branched alkyl chains having a general formula $C_nH_{2n+1}$, n ranges from about 6 to about 20, and ethoxylated alkyls having a general formula $R^3(OCH_2CH_2)_mOCH_2CH_2$—, where $R^3$ is a C1 to C4 alkyl group, and where m ranges from 0 to about 3; and where Y is selected from the group consisting of H, OH, and alkoxyl groups.

14 Claims, 11 Drawing Sheets

(56) References Cited

OTHER PUBLICATIONS

Z. Huang et al., "The syntheses, characterization and properties of some metallophthalocyanine complexes substituted by (N-(2-hydroxyethyl)piperazine)-N'-2-ethane sulfonic acid (HEPES)," Dyes & Pigments, vol. 77 (2008) 584-589.
Y. Tian et al., "2-(2'-Hydroxyphenyl)benzoxazole-Containing Two-Photon-Absorbing Chromophores as Sensors for Zinc and Hydroxide Ions," Chem. Maters., vol. 20 (2008) 1977-1987.
S Sumalekshmy et al., "Design of Emission Ratiometric Metal-Ion Sensors with Enhanced Two-Photon Cross Section and Brightness," JACS, vol. 129 (2007) 11888-11889.
S. J. K. Pond et al., "Metal-Ion Sensing Fluorophores with Large Two-Photon Absorption Cross Sections: Aza-Crown Ether Substituted Donor-Acceptor-Donor Distyrylbenzenes," J. Am. Chem. Soc., vol. 126 (2004) 9291-9306.
D. M. Nguyen et al., "Selective Fluorescence Sensing of Zinc and Mercury Ions with Hydrophilic 1,2,3-Triazolyl Fluorene Probes," Chem. Mater., vol. 22 (2010) 3472-3481.
A. Bhaskar et al., "Zinc Sensing via Enhancement of Two-Photon Excited Fluorescence," J. Phys. Chem. C., vol. 111 (2007) 14607-14611.
M. Pawlicki et al., "Two-photon absorption and the design of two-photon dyes," Angewandte Chemie, Int'l Ed., vol. 18 (2009) 3244-3266.
G. S. He et al., "Multiphoton absorbing materials: molecular designs, characterizations,and applications," Chem. Rev., vol. 108 (2008) 1245-1300.
R. Kannan et al., "Diphenylaminofluorene-based two-photon-absorbing chromophores with various pi-electron acceptors," Chem. Mater., vol. 13 (2001) 1896-1904.
S. J. Jhaveri et al., "Direct three-dimensional microfabrication of hydrogels via two-photon lithography in aqueous solution," Chem. Mater., vol. 21 (2009) 2003-2006.
K. D. Belfield et al., "Multiphoton-absorbing organic materials for microfabrication, emerging optical applications and non-desctructive three-dimensional imaging," J. Phys.Org. Chem., vol. 13 (2000) 837-849.
L-S Tan et al., "Two-photon absorbing molecules of donor-acceptor type with multi-alkyl substituted diarylamino groups," U.S. Appl. No. 15/711,084, filed Sep. 21, 2016.

PIPERAZINE-CONTAINING TWO-PHOTON ABSORBING COMPOUNDS

Pursuant to 37 C.F.R. § 1.78(a)(4), this application claims the benefit of and priority to prior filed co-pending Provisional Application Ser. No. 62/474,457, filed Mar. 21, 2017, which is expressly incorporated herein by reference.

RIGHTS OF THE GOVERNMENT

The invention described herein may be manufactured and used by or for the Government of the United States for all governmental purposes without the payment of any royalty.

FIELD OF THE INVENTION

The present invention relates to two-photon active compounds, and more particularly to piperazine-containing two-photon active compounds, as well as methods of making same.

BACKGROUND OF THE INVENTION

Two-photon absorption (TPA) occurs through the simultaneous absorption of two or more photons via virtual states in an absorbing medium. For a given chromophore, TPA processes take place at wavelengths much longer than the cut-off wavelength of its linear (single-photon) absorption. In the case of TPA, two quanta of photons may be absorbed from a single light source (degenerate TPA) or two sources of different wavelengths (non-degenerate TPA).

While multiphoton absorption processes have been known since 1931, the field remained dormant largely due to the lack of TPA-active materials with sufficiently large cross-sections. In the mid-1990s, several new classes of chromophores exhibiting very large effective TPA cross-section values, which are generally reported in GM=1×10$^{-50}$ cm$^4$ s photon$^{-1}$, were reported. In conjunction with the increased availability of ultrafast high-intensity lasers, the renewed interest has not only sparked a flurry of activities in the preparation of novel dye molecules with enhanced TPA cross-section values, but also many previously conceived applications based on TPA process in photonics and biophotonics are now enabled by these new chromophores. It is important to recognize the following features of two-photon materials technology: (a) upconverted emission, whereby an incident light at lower frequency (energy) can be converted to an output light at higher frequency, for instance, IR to UV-Vis up-conversion; (b) deeper penetration of incident light; (c) highly localized excitation allowing precision control of in-situ photochemical events in the absorbing medium, thereby minimizing undesirable activities such as photodegradation or photobleaching; and (d) fluorescence when properly manipulated allows information feedback. It is anticipated that further ingenious utilization of these basic characteristics will lead to new practical applications, in addition to those already under investigation, e.g., fluorescence imaging, data storage, eye and sensor protection, microfabrication of microelectromechanical systems (MEMS), photodynamic therapy, etc.

In recent years, an intense area of applied photonics research is focused on the utilization of TPA materials in ion sensing and assessment. One of the ion-assay techniques involves two-photon excitation fluorescence microscopy (TPEM). In comparison to traditional microscopy based on one-photon, i.e. UV-Vis-based, processes, TPEM in conjunction with TPA chromophores offers the aforementioned advantages such as increased penetration depth, 3D resolution, reduced phototoxicity, and low background fluorescence. Although these advantages of TPA materials as ion sensors are obvious, the selectivity and sensitivity with respect to environmental conditions, for example pH condition, still need to be improved.

Accordingly, there is a need for new TPA compounds, as well as methods of making the same.

SUMMARY OF THE INVENTION

The present invention overcomes one or more of the foregoing problems and other shortcomings, drawbacks, and challenges of existing two-photon absorbing compounds. While the invention will be described in connection with certain embodiments, it will be understood that the invention is not limited to these embodiments. To the contrary, this invention includes all alternatives, modifications, and equivalents as may be included within the spirit and scope of the present invention.

Thus, in accordance with an embodiment of the present invention, a two-photo active compound is provided having a general structural formula:

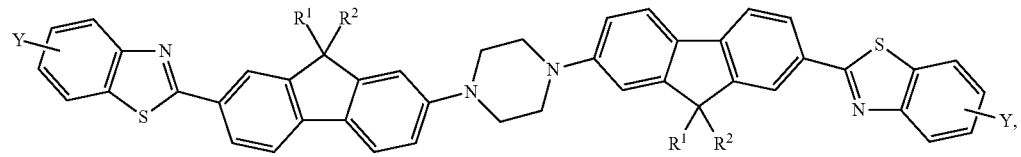

where $R^1$ and $R^2$ are independently selected from the group consisting of linear or branched alkyl chains having a general formula $C_nH_{2n+1}$ where n ranges from about 6 to about 20, and ethoxylated alkyls having a general formula $R^3(OCH_2CH_2)_mOCH_2CH_2$—, where $R^3$ is a C1 to C4 alkyl group, and where m ranges from 0 to about 5; and wherein Y is selected from the group consisting of H, OH, and alkoxyl groups.

In accordance with another embodiment of the present invention, a method of synthesizing the two photon compound is provided. The method comprises bis-substituting a 2,7-dihalofluorene compound to form a 9,9-disubstituted-2,7-dihalofluorene compound having a general formula:

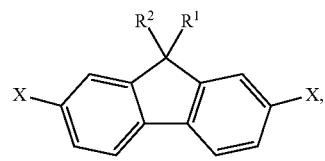

wherein X is I, Br, or Cl. The method may further include mono-formylating the 9,9-disubstituted-2,7-dihalofluorene compound to form a 9,9-disubstituted-2-halo-7-formyl-fluorene compound having a general formula:

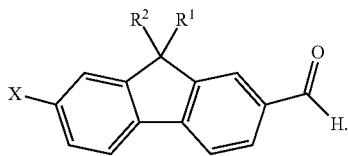

The method may further include reacting the 9,9-disubstituted-2-halo-7-formyl-fluorene compound with an ortho-aminothiophenol compound to form a 9,9-disubstituted-2-halo-7-benzothiazole-fluorene compound having a general formula:

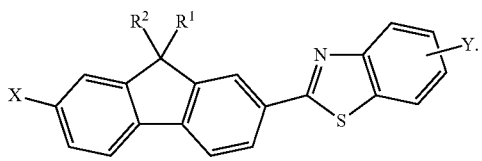

And the method may also include reacting the 9,9-disubstituted-2-halo-7-benzothiazole-fluorene compound with piperazine to form the two-photo active compound.

Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention. It will be appreciated that for purposes of clarity and where deemed appropriate, reference numerals have been repeated in the figures to indicate corresponding features.

It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

DETAILED DESCRIPTION OF THE INVENTION

The composition and synthesis of a series of two-photon active compounds with quadrupolar structure and bearing an N,N'-piperazinyl moiety serving as the electron donating core, 9,9-disubstituted-fluorenyl as π-bridge, and 2-benzothiazolyl as the terminal electron acceptor are described. The presence of a piperazine core, which serves as chelation site, is shown to enable characteristic but distinctly different fluorescent response of the subject molecules in the presence of proton and transition metal ions.

Figure 1:
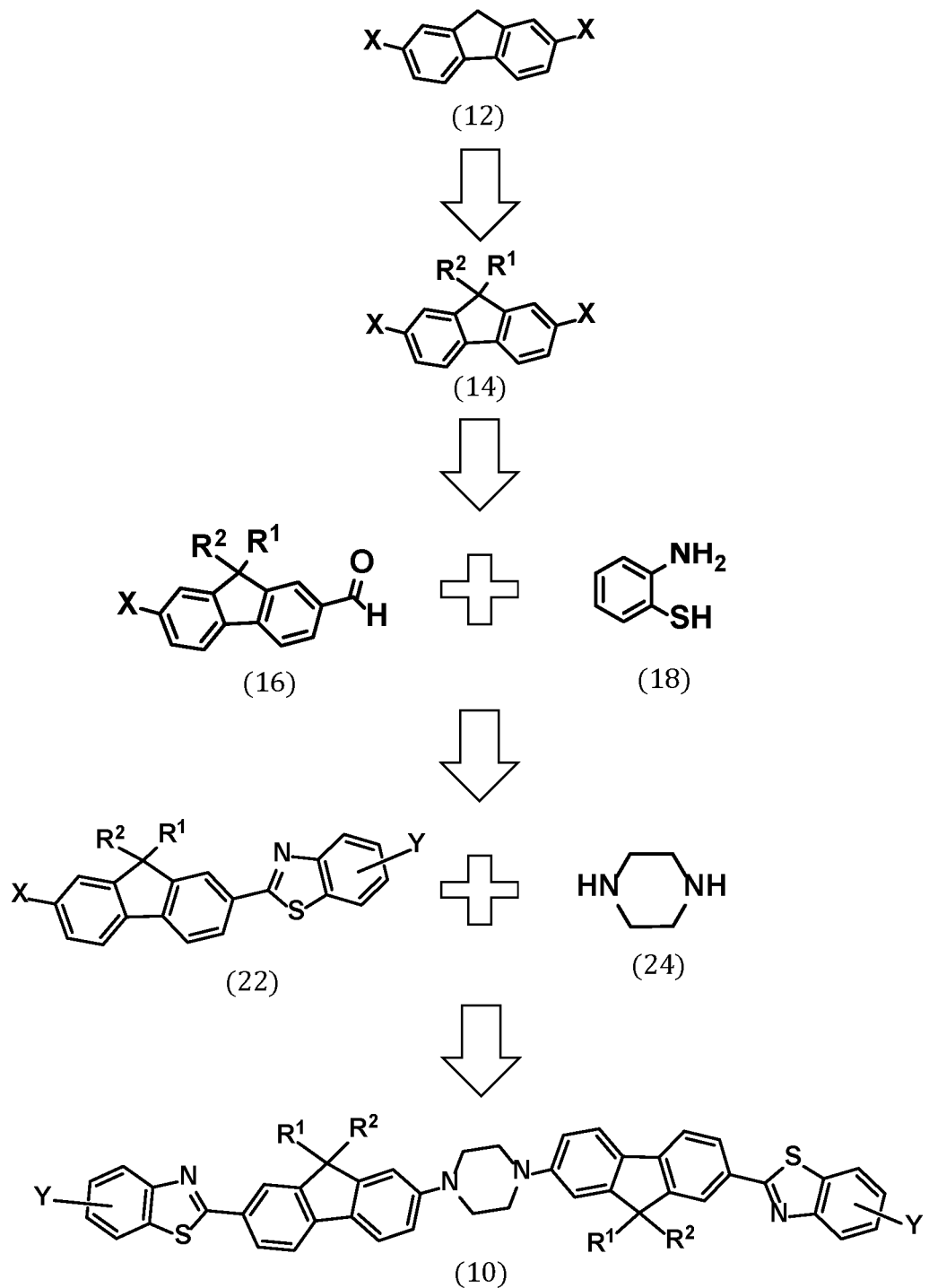
FIG. 1 is a schematic showing a retrosynthetic strategy for synthesizing a two photon active compound, in accordance with an embodiment of the present invention.

In accordance with an embodiment of the present invention and in reference to FIG. 1, a class of two photon active (TPA) compounds is provided, the TPA compounds (10) having a general formula:

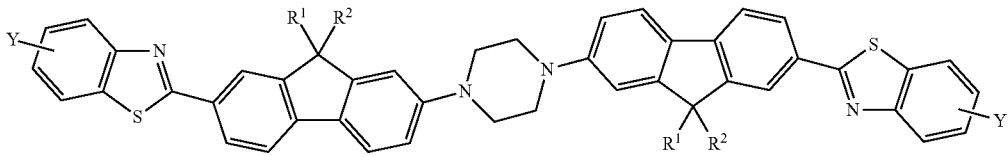

where $R^1$ and $R^2$ are independently selected from the group consisting of linear or branched alkyl chains having a general formula $C_nH_{2n+1}$ where n ranges from about 6 to about 20, and ethoxylated alkyls having a general formula $R^3(OCH_2CH_2)_mOCH_2CH_2$—, where $R^3$ is a C1 to C4 alkyl group, and where m ranges from 0 to about 5; and wherein Y is selected from the group consisting of H, OH, and alkoxyl groups.

In accordance with an embodiment, $R^1$ and $R^2$ are independently selected from the group consisting of linear or branched alkyl chains having a general formula $C_nH_{2n+1}$, and n ranges from about 6 to about 20. For example, about 8 to about 18, or about 5 to about 15. In one aspect, $R^1$ and $R^2$ may be the same group. In another aspect, $R^1$ and $R^2$ may be the same and selected from ethyl, 3-7-dimethyloctyl, n-decyl, or 2-ethylhexyl.

In accordance with another embodiment, $R^1$ and $R^2$ are independently selected from ethoxylated alkyls having a general formula $R^3(OCH_2CH_2)_mOCH_2CH_2$—, where $R_3$ is a methyl or ethyl group, and where m ranges from 0 to about 5. For example, m may be in a range from about 0 to about 3, or m may be 1.

In accordance with another embodiment, Y is H. In another embodiment, Y is $OCH_3$ or $OCH_2CH_3$. In yet another embodiment, Y is OH.

In one example, Y is H, and $R^1$ and $R^2$ are both ethyl, 3-7-dimethyloctyl, n-decyl, or 2-ethylhexyl.

With continued reference to FIG. 1 and in accordance with another embodiment of the present invention, a method of synthesizing the two photon compound (10) is provided. The method comprises bis-substituting a 2,7-dihalofluorene compound (12) to form a 9,9-disubstituted-2,7-dihalofluorene compound (14) having a general formula:

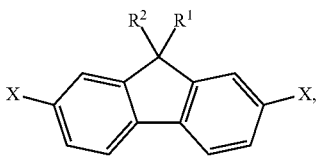

wherein X is I, Br, or Cl.

In accordance with another embodiment, the method may further include mono-formylating the 9,9-disubstituted-2,7-dihalofluorene compound (14) to form a 9,9-disubstituted-2-halo-7-formyl-fluorene compound (16) having a general formula:

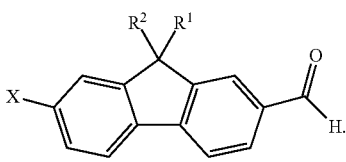

In accordance with another embodiment, the method may further include reacting the 9,9-disubstituted-2-halo-7-formyl-fluorene compound (16) with an ortho-aminothiophenol compound (18) to form a 9,9-disubstituted-2-halo-7-benzothiazole-fluorene compound (22) having a general formula:

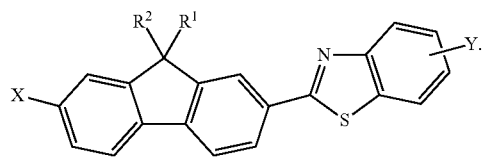

In accordance with yet another embodiment, the method may also include reacting the 9,9-disubstituted-2-halo-7-benzothiazole-fluorene compound (22) with piperazine (24) to form the two-photo active compound (10).

Figure 2:
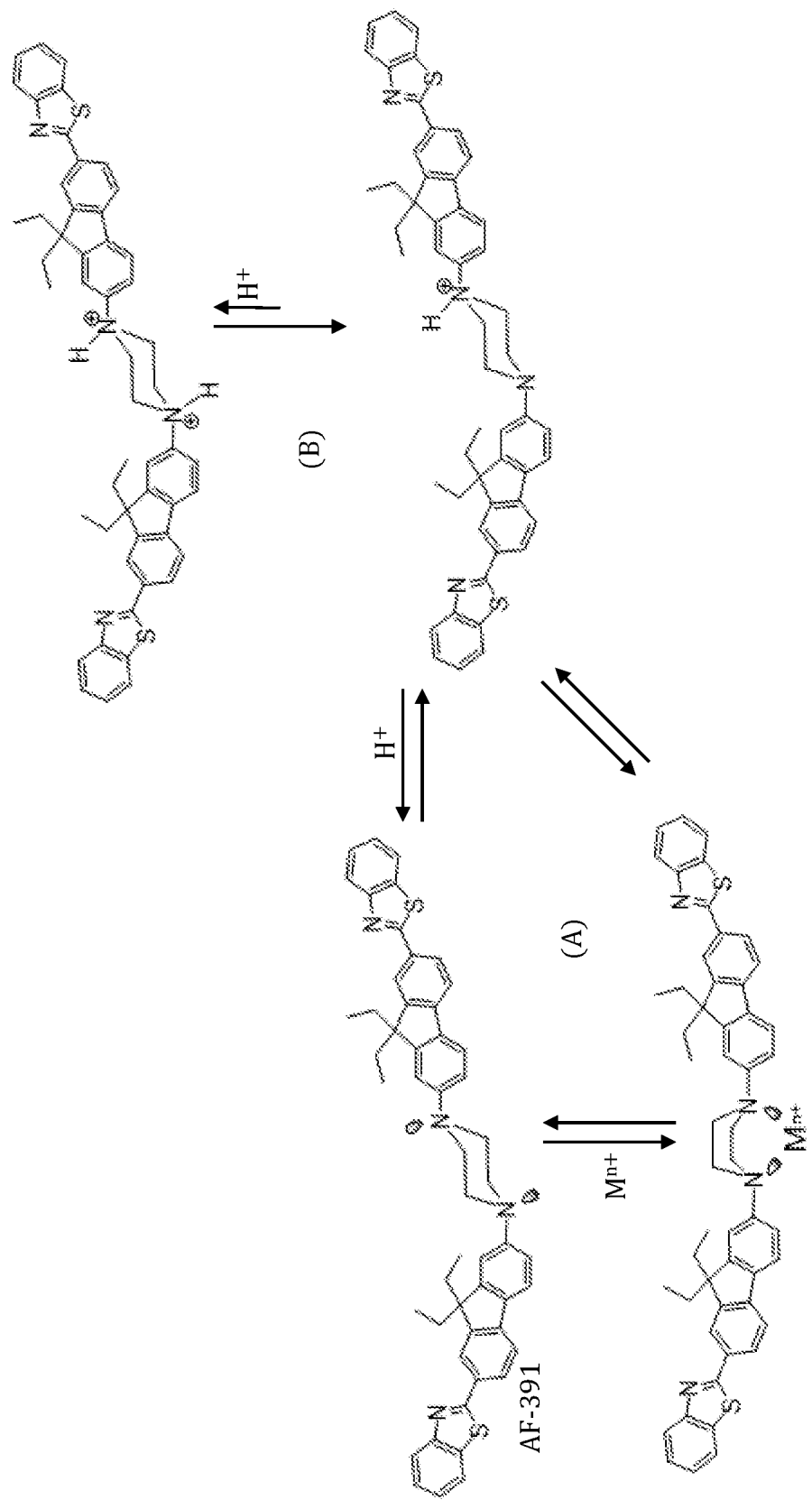
FIG. 2 is a schematic showing Lewis acid complexation or protonation equilibrium of exemplary two photon active compounds (e.g., AF391-XYZ) in 1:1 molar ratio.

In reference to FIG. 2, in accordance with another embodiment, the two photon active (TPA) compounds (10) may be combined with a Brønsted acid or a Lewis acid comprising a transition metal ion to form a salt or complex of the two-photo active compound. Exemplary Brønsted acids include, but are not limited to, strong acids such as sulfuric acid, hydrochloric acid, or trifluoromethanesulfonic acid, or weaker acids such as p-toluenesulfonic acid, trifluoroacetic acid, or acetic acid. Exemplary Lewis acids include, but are not limited to transition metal triflates (e.g., $Zn(O_3SCF_3)$) and transition metal hexafluorophosphates (e.g., $CuPF_6$).

The following examples illustrate particular properties and advantages of some of the embodiments of the present invention. Furthermore, these are examples of reduction to practice of the present invention and confirmation that the principles described in the present invention are therefore valid but should not be construed as in any way limiting the scope of the invention.

EXAMPLES

Figure 3:
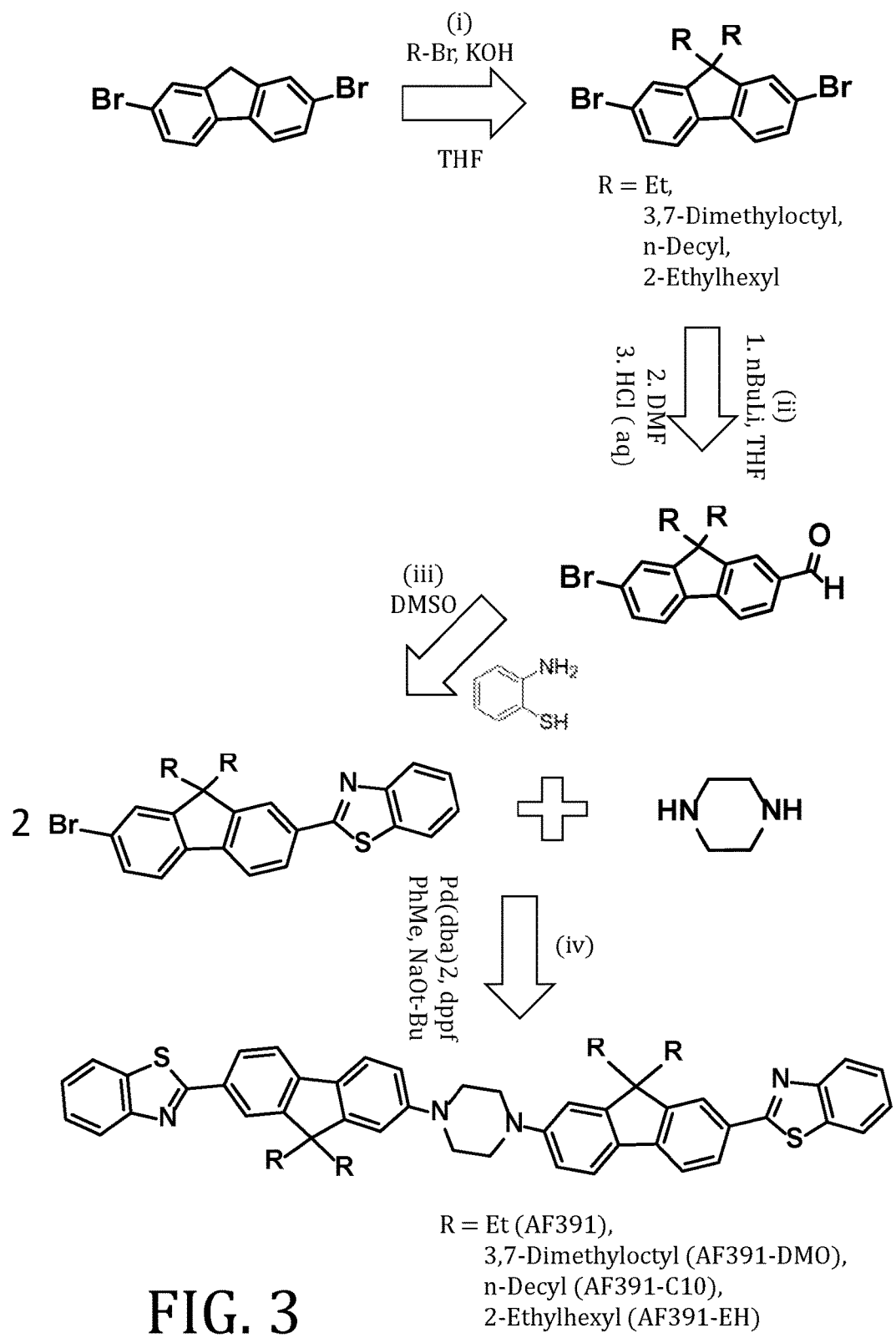
FIG. 3 is a schematic showing a four step synthetic sequence for synthesizing exemplary two photon active compounds (e.g., AF391-XYZ) in accordance with another embodiment of the present invention.

As shown in FIG. 3, an exemplary synthesis of two-photo active compound (10) (also herein referred to as AF391-XX) can be accomplished in 4 steps starting from commercially available 2,7-dibromofluorene via (i) double alkylation at 9,9-positions of 2,7-dibromofluorene (e.g., conducted with primary alkyl halide (preferably bromide or iodide to avoid the competitive olefin-forming elimination reaction of alkyl halide under relatively strong basic condition)); (ii) in a one-pot reaction, 2,7-dibromo-9,9-dialkylfluorene is first monolithiated by metal-halide exchange with n-butyllithium at −78° C. followed by the addition of N,N-dimethylformamide (DMF) as a formylating agent and quenching the lithium dimethylamide by-product with aqueous HCl; (iii) oxidative cyclo-dehydration of the corresponding aldehyde to benzothiazole product is conducted with 2-aminothiophenol in DMSO with heating; (iv) double Pd-catalyzed N-Aryl cross-coupling reaction of piperazine and two equivalents (with slight excess) of 2-bromo-7-(2-benzothiazolyl)-9,9-dialkylfluorene results in the formation of the subject two-photon absorbing chelating agent. Note that it is possible to induce water solubility by attaching water-solubilizing groups such as 2-(2-methoxyethoxy)ethyl or (2-(2-ethoxyethoxy)ethyl) group to the 9,9-positions reacting 2,7-disubstituted fluorene with 1-bromo-2-(2-methoxyethoxy)ethane or 1-bromo-(2-(2-ethoxyethoxy)ethane via double alkylation reaction (i) in Scheme 2.

Example 1

9,9-diethyl-2,7-dibromofluorene

To a mechanically stirred mixture of 2,7-dibromofluorene (66.5 g, 0.205 mol), powdered potassium hydroxide (56.0 g, 1.0 mol), potassium iodide (3.4 g) and DMSO (150 mL), cooled to 10° C., ethyl bromide (40 mL, 58.4 g, 0.536 mol) was added dropwise over 45 min. The mixture turned from red to light purple. After allowing the temperature to warm to 20° C., the mixture was left overnight to stir and poured into water, 77.0 g (98.7% yield), m.p. 144-153° C. The product was then recrystallized from hexane (550 mL) with charcoal treatment, and collected in two crops, m.p. 154-157° C. and 153-154° C., totaling 60.36 g (77.4% yield).

Example 2

9,9-diethyl-7-bromo-fluorene-2-carboxaldehyde

To a mechanically stirred solution of 9,9-diethyl-2,7-dibromofluorene (59.38 g, 0.1563 mol), in THF (325 mL), cooled in dry ice-ethanol bath, n-butyl lithium (104 mL of 1.6 M solution in hexanes, 0.1664 mol, 1.06 eq) was added dropwise over 25 min. After 20 min, DMF (17 mL, 0.22 mol) in THF (30 mL) was added, and the mixture was stirred in the cooling bath for 1.5 hrs, and outside the bath for 1 hr. The reaction was then cooled to 5° C., and treated with hydrochloric acid (12.5 mL of concentrated hydrochloric acid diluted with 50 mL water). The mixture was diluted with 200 mL of toluene, and the aqueous phase was separated and extracted with 200 mL of toluene. The combined organic phase was washed with dilute sodium bicarbonate solution, dried over magnesium sulfate, and concentrated. The residual solids were recrystallized from heptane-ethyl acetate (9:1), to get colorless solids, 40.29 g (78.4% yield) m.p. 126-128° C. The mother liquor after chromatography over 150 g silica gel, elution with 1:1 heptane-toluene, and trituration of residual solids in hexanes gave additional product, 6.56 g (12.8% yield, total 91% yield), m.p. 126-128° C. Mass Spectrum (m/z): 328, 330, (M$^+$). A sample for analysis was prepared by recrystallization from hexanes, m.p. 127-129° C.

Example 3

2-(7-bromo-9,9-diethylfluoren-2-yl)benzothiazole

A mixture of 9,9-diethyl-7-bromo-fluorene-2-carboxaldehyde (49.35 g, 0.15 mol), 2-aminothiophenol (20 mL, 0.187 mol, 1.25 eq), and DMSO (110 mL) was heated in an oil bath to a bath temperature of 195° C., held there for 45 min, and then poured into water. The separated solids were collected, reslurried in 1:4 acetic acid-water (1000 mL) filtered, and washed with water and dilute sodium bicarbonate solution. These solids, 80.05 g, were then reslurried in hot ethanol (600 mL), cooled, and filtered to get the product benzothiazole, 45.69 g, m.p. 133.6-135° C. An additional 6.6 g, m.p. 134.6-135.5° C., was obtained by chromatography of the ethanol filtrate. Total recovery was 52.29 g (80.3% yield). Mass Spec: m/z 433, 435, (M$^+$).

Example 4

Synthesis of 2,7-dibromo-9,9-di-n-decyl-9H-fluorene

To a 2 L three-necked round bottom flask equipped with mechanical stir, nitrogen inlet and outlet, 81.00 g (0.250 mol) 2,7-dibromo-9H-fluorence and 500 mL THF were charged. After the 2,7-dibromofluorence was dissolved, 58.9 g (0.525 mol) potassium t-butoxide was added in three batch. The mixture was turned from colorless to dark red immediately, 116.1 g (0.525 mol) of 1-bromodecane in 150 mL THF was added drop wise within 3.5 hrs. After addition completed, the mixture was stirred under nitrogen for 2 hrs. Potassium salts was removed through filtration. The filtrate was concentrated under vacuum to give yellow viscous oil. The final product was purified by silica gel chromatography using hexanes as eluent. 137.1 g product was obtained as waxy crystals, 90.7% isolated yield, m.p. 37.8-39.0° C.

Example 5

7-bromo-9,9-di-n-decyl-9H-fluorene-2-carboxaldehyde

To a 1 L three-necked round bottom flask equipped with mechanical stir, nitrogen inlet and outlet, 96.73 g (0.160 mol) 2,7-dibromo-9,9-di-n-decyl-9H-fluorene and 350 mL anhydrous THF were charged. After the mix was cooled by a dry ice/2-propanol bath to −80° C., 100 mL 1.6 M n-butyllithium in hexanes was added drop wise within 1 hr. After addition of butyllithium, the mixture was stirred at −80° C. for 30 min before 17 mL (0.219 mol) N,N-dimethylformate was added. The mixture was stirred at −80° C. for 30 minutes, then warmed up to 5° C. slowly. After cooled the mixture in ice-water bath, 30 mL 36.5% hydrochloric acid was added, then, the mixture was stirred for 30 min. Organic layer was separated and water layer was extract with 200 mL heptane for three times. The organic layer was combined and washed with brine and then DI water, then dried over anhydrous sodium sulfate. The solvents were removed under vacuum to give crude product. The product was purified by silica gel chromatography using heptane then mixture of heptane and toluene (5/1 v/v) as eluent. 60.5 g product was obtained as waxy crystals, 68.2% isolated yield, m.p. 42.5-44.5° C. $^1$H NMR (CDCl$_3$): δ=10.06 (s,1H), 7.85-7.87 (m, 2H), 7.79-7.81(d,1H), 7.64-7.62(d,1H), 7.49-7.52(m,1H), 1.91-2.05(m,4H), 1.02-1.27(m,28H), 0.83-0.86(t,6H), 0.51-0.61(m,4H).

Example 6

(7-bromo-9,9-di-n-decyl)-9H-fluoren-2-yl)benzothiazole

To a 100 mL round bottom flask equipped with stir bar and condenser, 4.43 g (8.00 mmol) 7-bromo-9,9-di-n-decyl-9H-fluorene-2-carboxaldehyde, 1.25 g (10 mmol) 2-aminothiophenol and 8 mL dimethy sulfoxide were charged. The mixture was heated to 160° C. and held for 1 hr. After cooled to room temperature, the mixture was poured into 100 mL mixture of acetic acid and water (1:4 v/v) and extracted by 100 mL hexanes for three times. The crude product was obtained after solvents were removed under vacuum as viscous liquid, which was further purified by silica gel chromatography using mixture of heptane and toluene (v/v 5/1) as eluent. 3.67 g final product was obtained as light yellow solids, 69.6% isolated yield, m.p. 70.6-71.7° C.

Example 7

Racemic dihydrocitronellyl bromide (1-bromo-3,7-dimethyloctane)

Concentrated sulfuric acid (17 mL) was added to 48% hydrobromic acid (100 mL) with stirring, and then 3,7-dimethyloctanol (dihydrocitronellol, Aldrich, 67 mL, 100 g) was added to the mixture. The mixture was then heated to 120-125° C., and kept at this temperature for 3 hrs. The reaction was cooled, and extracted into heptane (300 mL). The heptane layer was washed with hydrochloric acid, water, sodium bicarbonate solution, dried and concentrated to leave an oil, 81.5 g. This oil was distilled under vacuum at a bath temperature of 120-125° C., to afford the bromide product as an oil, b.p. 85-87° C./10 mmHg, 78.2 g, 100% yield. Mass Spec: m/z 220,222 ($M^+$).

Example 8

Racemic and Meso-9,9-bis(3,7-dimethyloctyl)-2,7-dibromofluorene

To a mechanically stirred mixture of 2,7-dibromofluorene (58.32 g, 0.18 mol), potassium iodide (3.0 g, 18 mmol), potassium hydroxide (50.4 g, 0.9 mol) and DMSO (150 mL), cooled in ice-water to 15° C., dihydrocitronellyl bromide (86.8 g, 0.392 mol) was added, and the mixture was stirred at room temperature for 18 hrs. The mixture was poured into water, and the product was extracted into a mixture of 1:1 toluene-heptane. The organic phase was washed with water, dried, and concentrated. The residual oil was refluxed with pyridine for 18 hrs to quarternize any unreacted bromide, and the mixture was diluted with toluene-heptane, and the organic phase was washed with water, dried, and concentrated. The residual orange oil was transferred to a column of 1050 g of alumina. Elution with hexanes (1800 mL) gave the product, 102.25 g, 94% yield, as a colorless oil. Mass Spec: m/z 602,604,606 ($M^+$).

Example 9

7-bromo-9,9-bis(3,7-dimethyloctyl)-9H-fluorene-2-carbaldehyde

To a mechanically stirred solution of 2,7-dibromo-9,9-bis (2,7-dimethyloctyl)-fluorene (51.4 g, 0.085 mol), in THF (400 mL), cooled in a dry-ice acetone bath, a solution of t-butyl lithium (1.7 M in pentane, 102 mL, 0.173 mol) was added over 17 min. After 22 min, a solution of DMF (15 mL, 0.19 mol) in THF (20 mL) was added. The cooling bath was removed after 45 min, and after 2 hrs, hydrochloric acid (25 mL diluted with 75 mL water). Extractive work up with toluene gave a liquid, 47.71 g, a mixture of mono and dialdehydes. EIMS: m/z 552,554 ($M^+$, bromo aldehyde), 502 ($M^+$, dialdehyde). This was chromatographed over alumina. Elution with heptane gave pure bromo aldehyde as a liquid, 14.57 g (31% yield). EIMS: m/z 552,554 ($M^+$).

Example 10

1,4-bis(7-(benzothiazol-2-yl)-9,9-diethyl-9H-fluoren-2-yl)piperazine (AF391)

To a 50 mL single necked round bottom flask equipped with a condenser, a nitrogen inlet and a magnetic stirrer-bar, 0.868 g (2.00 mmol) of 2-(7-bromo-9,9-diethylfluoren-2-yl) benzothiazole, piperazine (86.0 mg, 1.00 mmol), sodium tert-butoxide (0.230 g, 2.40 mmol), 2-dicyclohexylphosphino-2',4',6'-triisopropylbiphenyl, "Xphos" (24.0 mg, 0.05 mmol) and toluene (4 mL) were charged. After three cycles of quick evacuation (a few seconds) and back-filling with nitrogen, 6.00 mg (0.01 mmol) of bis(dibenzylideneacetone) palladium(0), Pd(dba)$_2$ was added to the reaction mixture. The mixture was heated to 100° C. and held at this temperature for 16 hrs before being allowed to cool to r.t. After solvent had been removed under vacuum, 50 mL water was added to the solids to form a suspension after trituration with a spatula. The water-insoluble solids were harvested by filtration, and air dried. The crude product further purified by column chromatography with silica gel as stationary phase and methylene chloride as eluent. Thus, 0.490 g (61.9% isolated yield) of the desired product was obtained as bright yellowish green crystals after stripping off methylene chloride on a rotavap, m.p. greater than 320° C. $^1$H NMR (400 MHz, CDCl$_3$): δ=8.07-8.09 (m,4H), 7.99-8.02(dd, 2H), 7.90-7.92(d. 2H), 7.67-7.70(dd,4H), 7.47-7.51(t, 2H), 7.35-7.39(t, 2H), 6.97-7.03(m,4H), 3.50(s, 8H), 2.01-2.36(m, 8H), 0.36-0.40 (t, 6H). Elemental Analysis Calculated for $C_{58}H_{48}N_4S_2$: C, 78.75; H, 6.10; N, 7.06%. Found: C, 78.68; H, 6.07; N, 7.04%.

Example 11

1,4-bis(7-(benzothiazol-2-yl)-9,9-di(2-ethylhexyl)-9H-fluoren-2-yl)piperazine (AF391-EH)

To a 100 mL round bottom flask equipped with magnetic stir, nitrogen inlet and condenser, 2-(7-bromo-9,9-di(2-ethylhexyl)-9H-fluoren-2-yl)benzothiazole (6.68 g; 11.1 mmol), piperazine (0.465 g, 5.40 mmol), sodium tert-butoxide (1.5568 g, 16.2 mmol), Xphos (128.7 mg, 0.270 mmol) and Pd(dba)$_2$ (62.10 mg, 0.108 mmol) were charged After three cycles of quick evacuation (a few seconds) and back-filling with nitrogen, 50 mL of toluene was added to the reaction mixture. The mixture was heated to 85.0° C. and held at this temperature for 16 hours before being allowed to cool to r.t. The resulting reaction mixture was filtered, and the solid residues were washed with 100 mL of toluene. The filtrate was concentrated under vacuum to give a viscous liquid crude product, which was purified by column chromatography with silica gel as the stationary phase and heptane/toluene (1:2) as the eluent. After removal of eluent, a greenish yellow solid resulted. After recrystallization from heptane, 3.51 g of greenish yellow crystalline solid was obtained; 57.5% isolated yield, m.p 127.3-130.0° C. $^1$H NMR (400 MHz, CDCl$_3$): δ=8.03-8.09 (m,6H), 7.88-7.90 (d, 2H), 7.64-7.69(m,4H), 7.46-7.50(t,2H), 7.34-7.38(t,2H), 7.02 (br s,4H), 3.45(s,8H), 1.97-2.15(m,8H), 0.70-0.94(m, 38H), 0.51-0.61(m,22H). $^{13}$C NMR (100 MHz, CDCl$_3$) δ=168.88, 154.38, 152.71, 151.28, 150.80, 144.59, 134.92, 132.91, 130.45, 126.71, 126.13, 124.76, 122.91, 121.45, 120.90, 119.05, 115.97, 111.93, 55.05, 49.85, 44.58, 44.38, 34.69, 33.78, 28.27, 28.09, 27.13, 27.04, 22.78, 22.69, 14.10, 13.93, 10.51, 10.34. Elemental Analysis Calculated for $C_{76}H_{96}N_4S_2$: C, 80.80; H, 8.57; N, 4.96; S, 5.68%. Found: C, 80.82; H, 8.57; N, 4.95; S, 5.67%.

Examples 12

1,4-bis(7-(benzothiazol-2-yl)-9,9-di-n-decyl-9H-fluoren-2-yl)piperazine (AF391-C10)

To a 100 mL round bottom flask equipped with magnetic stir, nitrogen inlet and condenser, 2-(7-bromo-9,9-di-n-decyl)-9H-fluoren-2-yl)benzothiazole (3.670 g, 5.57 mmol), piperazine (0.234 g, 2.71 mmol), sodium tert-butoxide (1.070 g, 11.1 mmol), Xphos (64.6 mg, 0.270 mmol) and Pd(dba)$_2$ (31.0 mg, 0.054 mmol) were charged. After three cycles of quick evacuation (a few seconds) and back-filling with nitrogen, 27 mL of toluene was added to the mixture. The reaction mixture was heated to 90° C. and held at this temperature for 16 hrs before being allowed to cool to r.t. After filtration, the solid residues were washed with 100 mL of toluene. The combined filtrate was concentrated under vacuum to give a viscous liquid as crude product, which was purified by column chromatography with silica gel as the stationary phase and heptane/toluene (1/2) as the eluent. The isolated solids after column chromatography were further purified by recrystallization from heptane to give 2.30 g of greenish yellow crystals, 75.1% isolated yield, m.p. 95.5-98.5° C. $^1$H NMR (400 MHz, CDCl$_3$): δ=8.08-8.10 (m,4H), 7.99-8.01 (d,2H), 7.88-7.90(d, 2H), 7.64-7.68(m,4H), 7.46-7.50(t,2H), 7.34-7.38(t,2H), 6.98-7.01(m,4H), 3.49(s,8H), 1.96-2.14(m,8H), 1.05-1.24(m,56H), 0.80-0.84(t, 12H), 0.66-0.71(m,8H). $^{13}$C NMR (100 MHz, CDCl$_3$) δ=169.03, 154.32, 153.14, 151.72, 151.07, 144.50, 134.93, 132.64, 131.03, 127.20, 126.23, 124.89, 122.88, 121.49, 121.36, 121.01, 119.08, 115.13, 110.72, 55.42, 49.69, 40.51, 31.88, 30.02, 29.57, 29.29, 23.76, 22.66, 14.10%. Elemental Analysis Calculated for $C_{84}H_{112}N_4S_2$: C, 81.24; H, 9.09; N, 4.51; S, 5.16. Found: C, 81.37; H, 9.09; N, 4.73; S, 5.15%.

Example 13: 1,4-bis(7-(benzothiazol-2-yl)-9,9-di(3,7-dimethyloctyl)-9H-fluoren-2-yl)piperazine (AF391-DMO)

To a 100 mL round bottom flask equipped with magnetic stir, nitrogen inlet and condenser, 2-(7-bromo-9,9-bis(3,7-dimethyloctyl)-9H-fluoren-2-yl)benzothiazole, (6.753 g, 10.25 mmol), piperazine (0.4307 g, 5.0 mmol), sodium tert-butoxide (1.4415 g, 15.0 mmol), Xphos (119.2 mg, 0.250 mmol) and Pd(dba)$_2$ (57.5 mg, 0.10 mmol) were charged. After three cycles of quick evacuation (a few seconds) and back-filling with nitrogen, 25 mL of toluene was added. The reaction mixture was heated to 90° C. and held at this temperature for 16 hrs before being allowed to cool to r.t. After filtration, the solid residues were washed with 100 mL of toluene. The combined filtrate was concentrated under vacuum to give a viscous liquid as crude product, which was purified by column chromatography with silica gel as the stationary phase and heptane/toluene (1:2) as eluent. The product was greenish yellow semi-solids after solvents were removed under vacuum. The solids recrystallized upon standing in ethanol to give 4.85 g of greenish yellow crystals, 85.9% isolated yield, m.p. 119.0-123.0° C. $^1$H NMR (400 MHz, CDCl$_3$): δ=8.01-8.09(m,6H), 7.89-7.91 (d, 2H), 7.65-7.69(t,4H), 7.47-7.51(t,2H), 7.35-7.38(t,2H),6.97-7.02(m,4H), 3.48(s,8H), 1.98-2.12(m,8H), 1.38-1.42(m,4H), 0.56-1.16(m,72H). $^{13}$C NMR (100 MHz, CDCl$_3$) δ=168.96, 154.32, 152.99, 151.74, 150.95, 144.52, 134.90, 132.75, 131.03, 127.08, 126.17, 124.83, 122.89, 121.43, 120.97, 119.06, 115.29, 110.68, 55.20, 49.73, 39.19, 39.16, 37.75, 37.65, 36.73, 36.51, 32.86, 30.54, 30.45, 27.88, 24.62, 22.64, 22.55, 19.60, 19.45. Elemental Analysis Calculated for $C_{84}H_{112}N_4S_2$: C, 81.24; H, 9.09; N, 4.51; S, 5.16%. Found: C, 81.26; H, 9.07; N, 4.51; S, 5.14%.

It was observed that the members of the series with longer and branched dialkyl groups (e.g., 9,9-bis(n-decyl) (AF391-C10); 9,9-bis(3,7,dimethyloctyl) (AF391-DMO), or 9,9-bis(2-ethylhexyl) (AF391-EH)) have similar photophysical properties as AF391 (9,9-diethyl), but are more soluble than AF391, especially in less polar solvents. On the other hand, water-solubility can be imparted to the corresponding AF391 derivatives by 9,9-peglyation with low molecular weight poly(ethylene glycol) or PEG as represented by 2-(methoxyethoxy)ethoxy or 2-(2-ethoxyethoxy)ethoxy.

Figure 4:
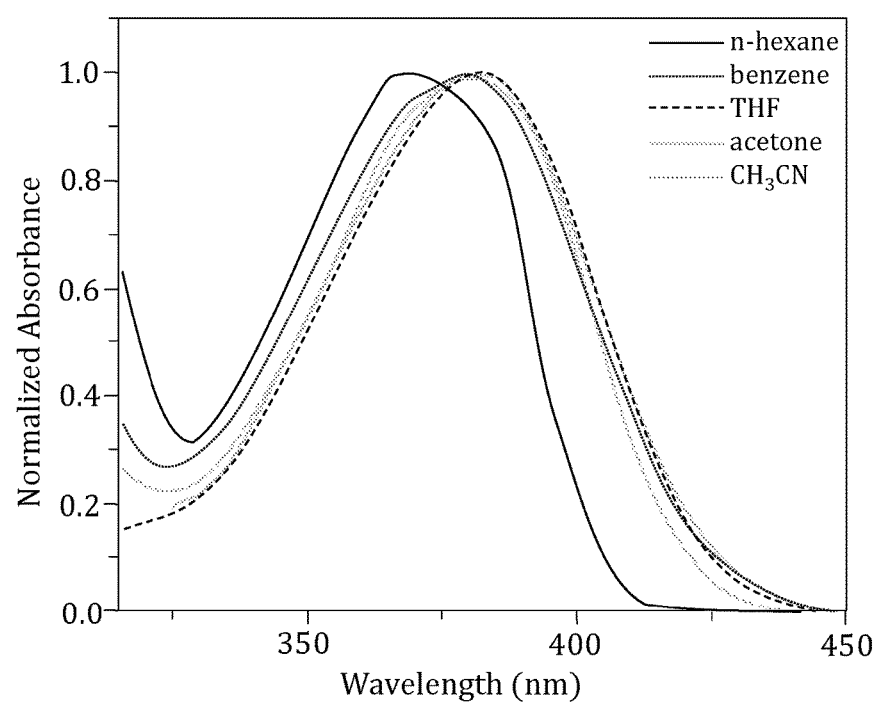
FIG. 4 is a plot of normalized absorption spectra versus wavelength (nm) of AF-391 in various solvents.
Figure 5:
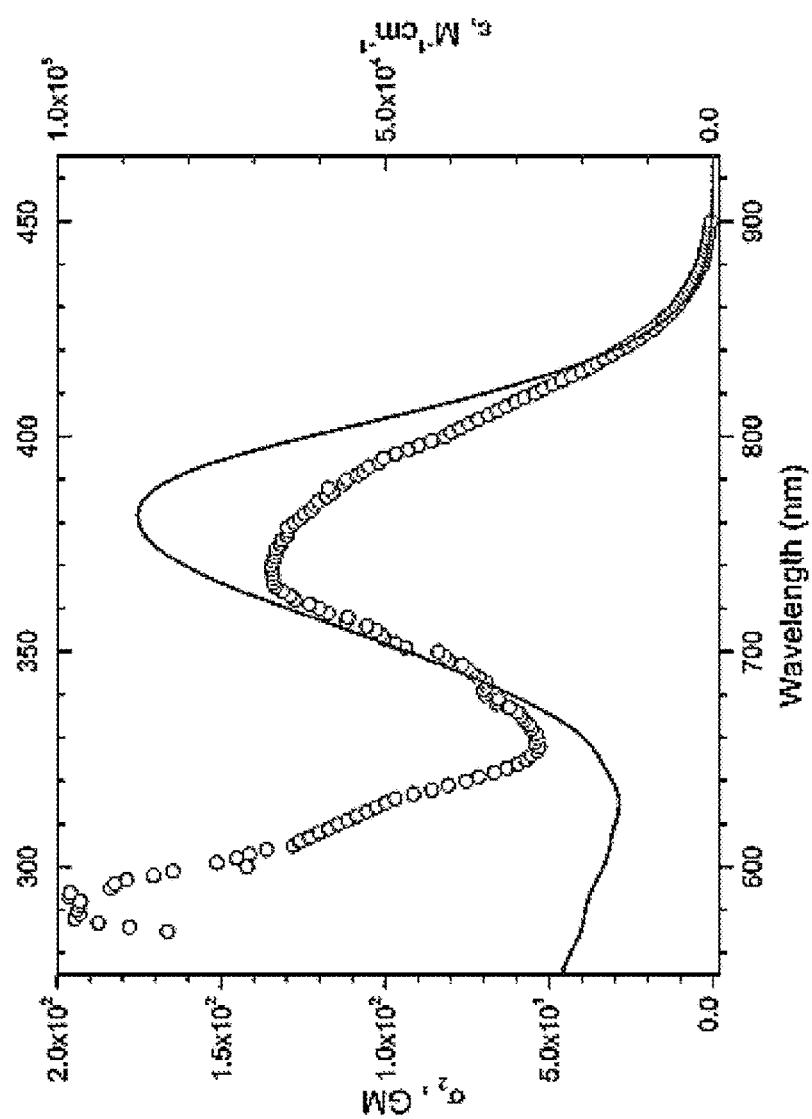
FIG. 5 is plot of two-photon (circles) and single photon (solid red) absorption spectra in THF, where the left and bottom axes relate to the two photon absorption spectrum, while the right and top are for the single photon absorption spectrum.

FIG. 4 shows normalized absorption spectra of AF-391 in five aprotic solvents (n-hexane, benzene, tetrahydrofuran (THF), acetone, and acetonitrile) with varying polarities. Absorption maxima are given in Table 1. In n-hexane the absorption spectrum shows slight structure, with a maximum at 368 nm and a noticeable shoulder around 380 nm. In the other four solvents, the spectra are very similar and undergo a bathochromic (or red) shift relative to that in n-hexane, and also broaden. The combined red-shift and broadening is a general indication of some ground-state intramolecular charge-transfer (ICT) character. Because of its lower polarity, the spectrum in benzene is not quite as broad as the other more polar solvents (THF, acetone and acetonitrile), suggesting slightly less ICT character, i.e., less propensity to charge separation in the ground state. Because the absorption spectra do not shift considerably (as in the emission spectra discussed below) with increasing polarity, the ground-state ICT is minimal. The molecule also shows good 2PA response (FIG. 5), with a broad 2PA absorption maximum at 736 nm with a peak 2PA cross section of $\sigma_2$=140 GM (GM=Goeppert-Mayer units, $10^{-50}$ cm$^4$ s photon$^{-1}$) and relatively large wavelength range (greater than 100 nm with useful $\sigma_2$>100 GM).

Figure 6:
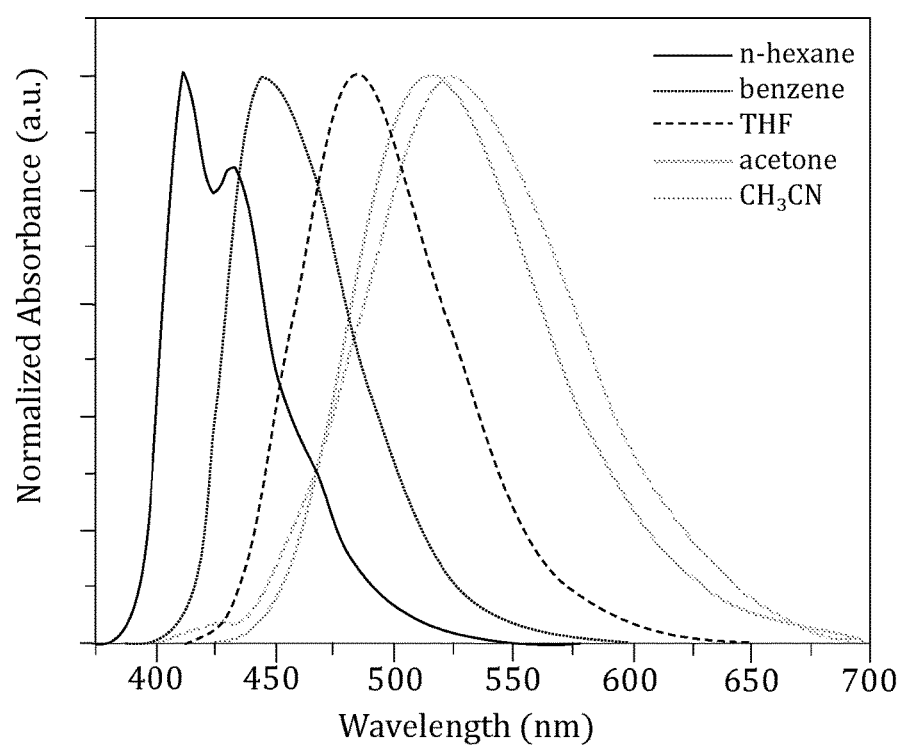
FIG. 6 is a plot of normalized emission spectra of AF-391 in various solvents, where excitation wavelength $(\lambda_{ex})$=390 nm

The emission spectra are shown in FIG. 6 and relevant photophysical properties are listed in Table 1. The spectra broaden and bathochromically shift with increasing polarity, indicating significant ICT character. The structured spectrum in n-hexane is attributed to a locally-excited (LE) state, which is relatively solvent independent because of little or no polarization during a purely n→π excitation. The ICT state is stabilized by increasing solvent polarity which leads to the "red-shift" in emission energies. For solvents n-hexane through acetone (i.e., in increasing polarity), the quantum yields decrease as the lifetimes increase, as observed for AF240 that differs structurally in having diphenylamine connected to the fluorene bridge. The cause of this is twofold. First, the nature of the state is changing from LE to ICT as the solvent polarity increases. Second, the charge-separation distance increases with solvent polarity, leading to a shorter radiative rate constant while the non-radiative rate constant remains relatively intact (Table 1). The emission signal in acetonitrile was too weak to obtain a reliable quantum yield and the lifetime became much shorter than that in the other solvents. The acetonitrile used was not dried, so quenching via hydrogen bonding from water at the central piperazine moiety likely occurs. This may also be the reason for the slight increase in the non-radiative rate constant observed in acetone.

TABLE 1

PHOTOPHYSICAL PROPERTIES OF AF391 IN VARIOUS SOLVENTS

| Solvent | $\lambda_{abs}$ (nm) | E ($M^{-1}cm^{-1}$) | $\lambda_{em}$ nm | Stokes shift ($cm^{-1}$) | $\Phi_{em}$ | τ (ns) | $k_r$ ($s^{-1}$) | $k_{nr}$ ($s^{-1}$) |
|---|---|---|---|---|---|---|---|---|
| n-hexane | 368 | | 412 | 2902 | 0.757 | 0.952 | 7.95 | 2.55 |
| benzene | 381 | | 447 | 3876 | 0.722 | 1.09 | 6.62 | 2.55 |
| THF | 384 | 216300 | 485 | 5423 | 0.591 | 1.40 | 4.22 | 2.92 |
| acetone | 382 | | 517 | 6836 | 0.210 | 1.52 | 1.38 | 5.20 |
| acetonitrile | 379 | | 524 | 7301 | — | 0.323 | — | — |

Figure 7:
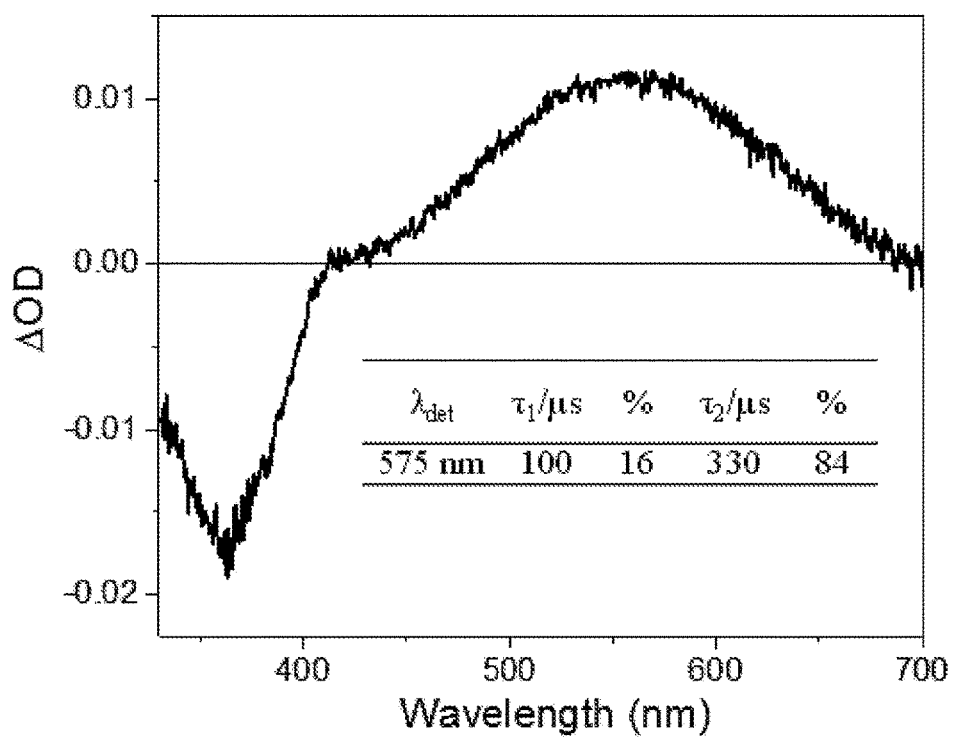
FIG. 7 is a plot of transient absorption spectrum of AF-391 in n-hexane 50 ns after excitation. [AF391]≈1.1 µM, $\lambda_{ex}$=355 nm.

The nanosecond transient absorption spectrum 50 ns after excitation (FIG. 7) shows a ground-state bleach at around 370 nm, with a broad, positive ΔOD signal observed from 410-700 nm with a maximum around 560 nm. The broad spectrum covering the visible region and stretching into the NIR is consistent with other AFX dyes and assigned as the excited-state triplet due to its long lifetime. A biexponential fit is observed with lifetimes of 100 μs (16%) and 330 μs (84%).

Figure 8:
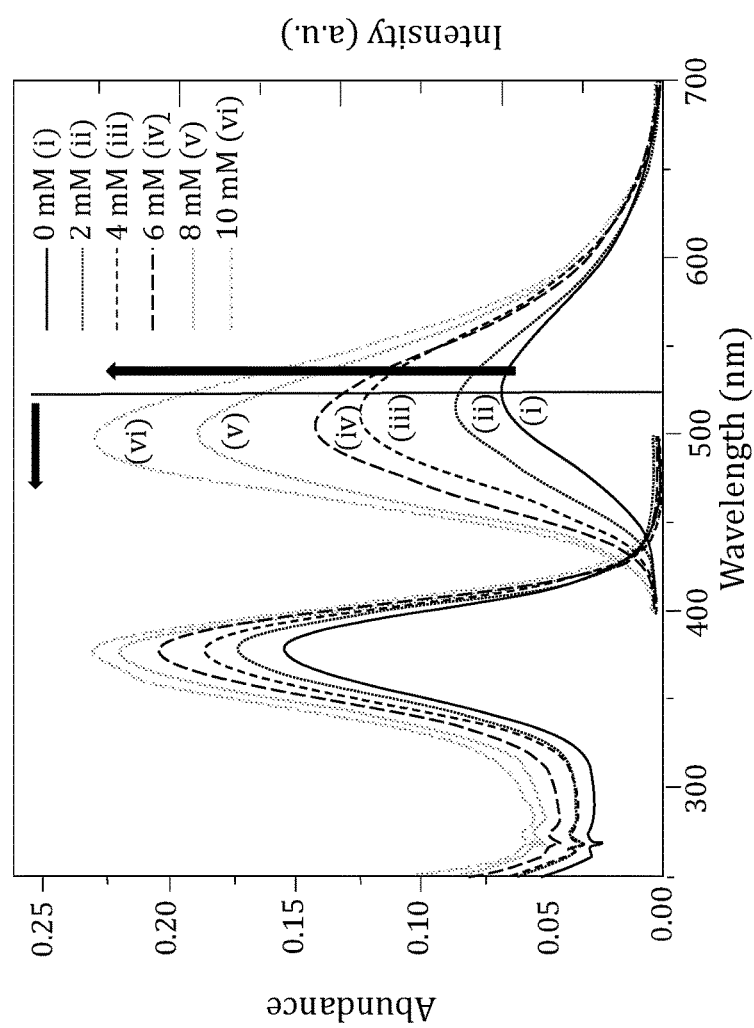
FIG. 8 is a plot of absorption (solid lines) and emission (dotted lines) spectra of AF-391 with varying $Zn(O_3SCF_3)_2$ in $CH_3CN$, where the concentration of AF-391 was approximately 0.72 µM, and the emission spectra, $(\lambda_{ex}$=390 nm), show blue-shifting and increasing intensity with increasing $[Zn^{2+}]$.
Figure 9:
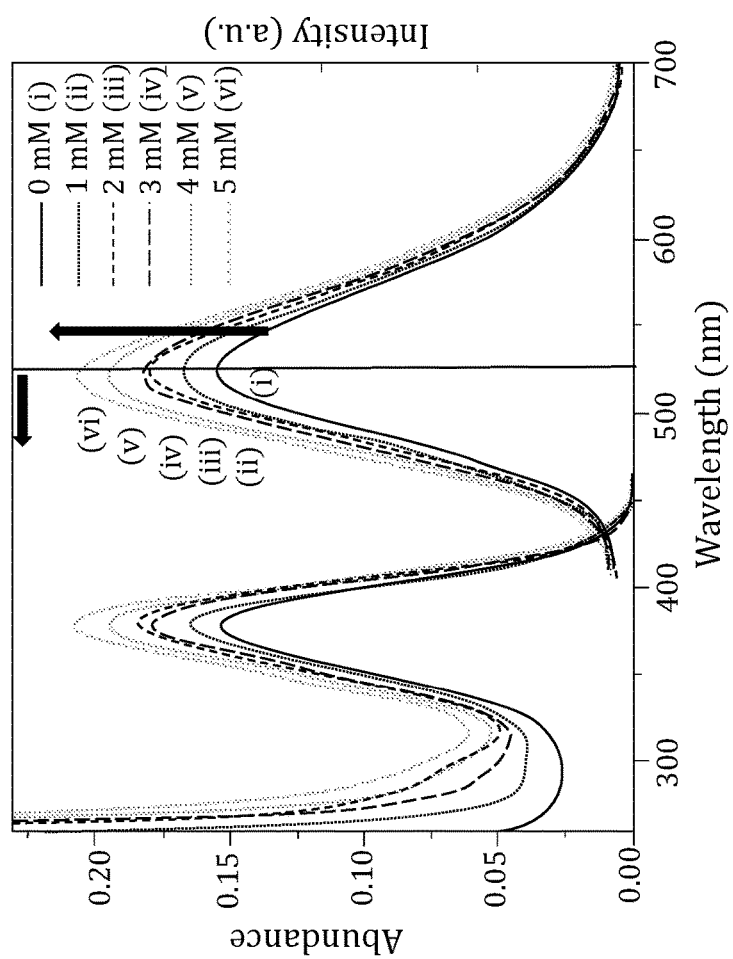
FIG. 9 is a plot of absorption (solid lines) and emission (dotted lines) spectra of AF-391 with varying $CuPF_6$ in $CH_3CN$, where the concentration of AF-391 was approximately 0.71 µM, and the emission spectra, $(\lambda_{ex}$=390 nm), show blue-shifting and increasing intensity with increasing $[Cu^+]$.

Absorption and emission spectra showing the effects of added Zn(O$_3$SCF$_3$)$_2$ and CuPF$_6$ to AF391 are shown in FIG. 8 and FIG. 9, respectively. Acetonitrile was chosen as a solvent as both AF391 and the metal salts were soluble, but the Zn and Cu complexes were only soluble to 10 and 5 mM, respectively. It should be noted that the individual Zn and Cu complexes have no absorption or emission signal in the region of interest. In both cases, addition of the metals leads to a hyperchromic shift in the absorption spectrum, a clear sign of ground-state complexation. In the case of Zn(II), a shoulder is also observed on the high energy side of the maximum once the concentration reaches 10 mM, but the same effect is not observed for Cu(I) (although only 5 mM could be obtained). It should be noted that the small offset observed in the Cu$^+$ spectra at 350 nm is due to an instrument grating change. The results indicate that AF391 is a good chelating molecule and that pre-association occurs in the ground state.

Like the absorption spectra, the emission spectra also increase in intensity with added metal ions. The spectra with Zn(II) show a remarkable increase along with a hypsochromic (blue) shift. In the case of Cu(I), the changes are not as impressive, as only a moderate increase in the emission intensity is observed with no shift in the maximum. However, it should be noted the Cu(I) concentration is half that of Zn$^{2+}$. Additionally, charge likely plays a large role here. The central piperazine is electron rich and donating in the ICT process. In the case of Zn(II), which is a relatively strong Lewis acid, the higher charge pulls electron density out of the piperazine moiety, and decreases the amount of ICT character in the complex. As indicated by the solvent dependent data, a decrease in the ICT extent leads to higher energy emission with larger quantum yields, which is the same effect observed here. The results indicate AF391 may be a more effective sensor for ions with a higher charge.

Figure 10:
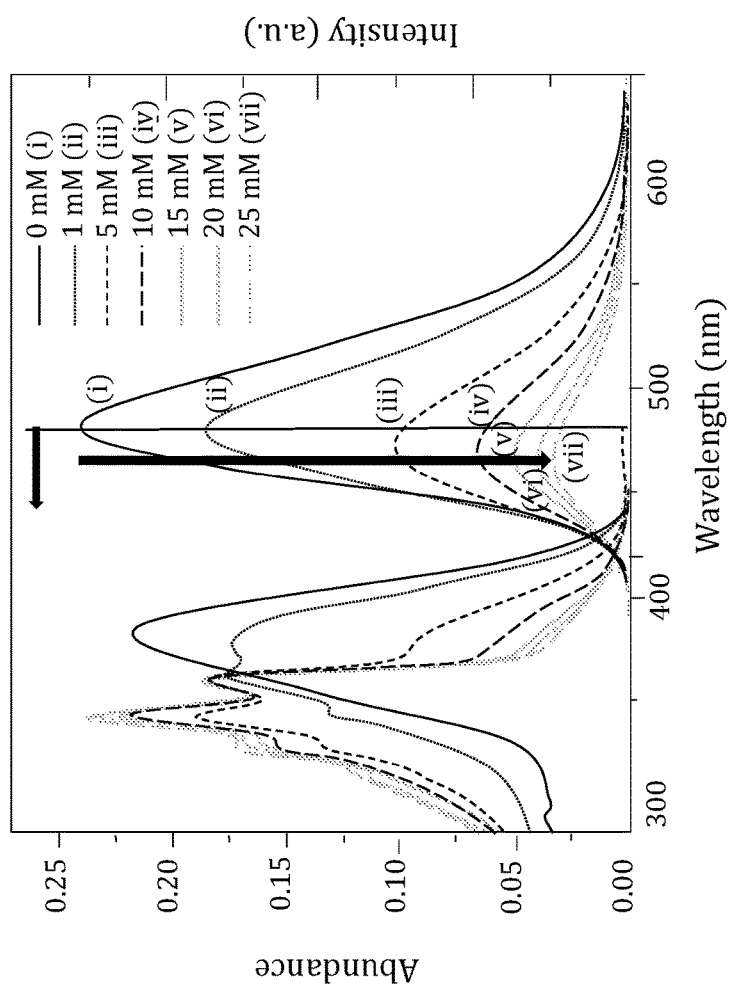
FIG. 10 is a plot of absorption (solid) and emission (dotted) spectra of AF-391 with varying p-toluenesulfonic acid in THF, where the concentration of AF-391 was approximately 1.0 µM, and the emission spectra, $(\lambda_{ex}$=390 nm), show blue-shifting and decreasing intensity with increasing $[H^+]$.
Figure 11:
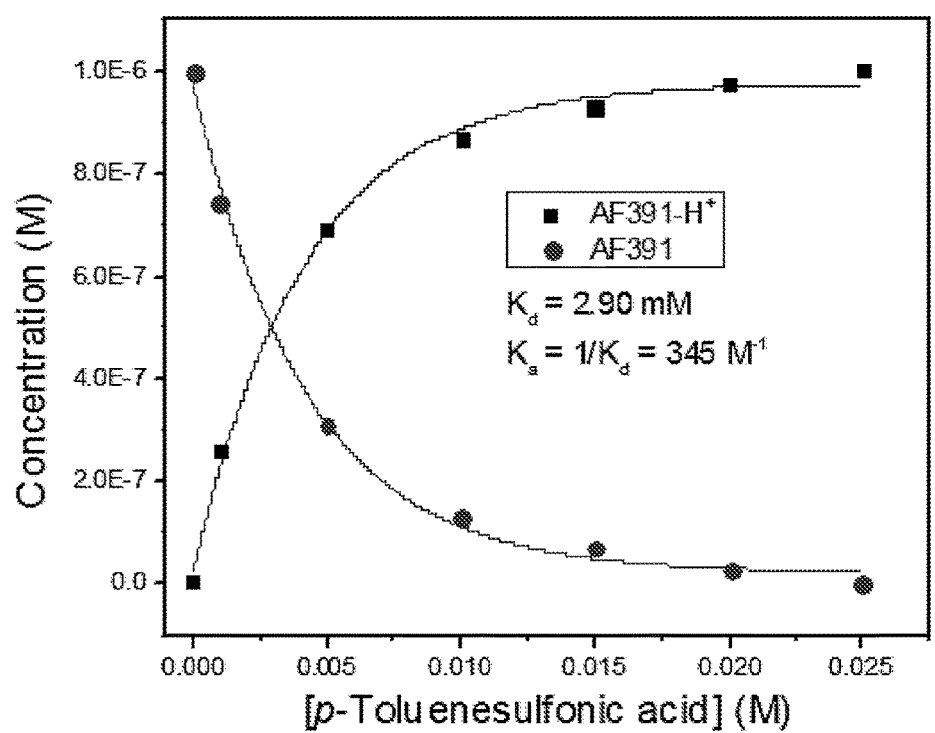
FIG. 11 is a plot showing changes in concentration of unprotonated AF-391 and protonated AF-391-H$^+$ as a function of increasing p-toluenesulfonic acid in THF.

When adding p-toluenesulfonic acid to AF391 in THF, much more dramatic ground state effects are observed than with the metal ions (FIG. 10). The absorption spectrum changes from being broad with a maximum at 384 nm to being structured with a maximum at 342 nm. An isosbestic point is observed around 361 nm, indicating two species are present, unprotonated AF391 and the protonated form (AF391-H). With 25 mM acid added, both the absorption and emission spectra stop changing. Knowing the initial concentration of AF391 and by assuming the spectrum at 25 mM is fully protonated, the extinction coefficient of AF391-H can be determined. Then, by knowing extinction coefficients of both species at two different wavelengths, the concentration of each can be determined as a function of added p-toluenesulfonic acid, and FIG. 11 can be generated. By using the point where the concentrations are equal, an association constant is obtain with Ka=345 M−1.

In another difference between acid and metal ion addition, the emission intensity is decreased (FIG. 9). The protonated species is still emissive (suggesting that not both nitrogens are protonated) as observed by the signal at 25 mM acid and is also at slightly higher energy than free AF391. The increase in emission intensity of the Zn and Cu complexes was explained due to a decrease in ICT character. The higher energy emission with added acid would also indicate a decrease in ICT, but the intensity goes down. This is likely caused by an increase in non-radiative decay pathways due to vibrational decay via the new H—N bond in the piperazine moiety. The results show the flexibility in using AF391 as an emissive ion sensor for both metals (increase in intensity) and protons (decrease in intensity).

Thus, embodiments of the present invention are related a series of fluorescent probing molecules (AF391-XYZ) based on the two-photon active dipolar AF240 has been designed and synthesized. AF391-XYZ has a unique feature of having central piperazine moiety that is basic and serves as a potential site for protonation and metal ion chelation (See FIG. 2). For example, addition of copper(I) hexafluorophosphate and zinc(II) triflate in acetonitrile indicate spectroscopically ground-state complexation with a shift in the emission maximum from 524 nm to 489 nm and 487 nm, respectively. The complexes Cu(II) and Zn(II) are more strongly emissive than the free AF391. On the other hand, while protonation of AF391, for example, by p-toluenesulfonic acid in tetrahydrofuran also blue-shifts the emission maximum, the intensity of the protonated AF391 is quenched. The contrast in fluorescent behaviors in the presence of metal ions or protons would encourage the potential of these dyes as two-photon probes/tags for sensing of cationic species, especially in distinguishing proton and metal ions in low pH environment.

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the scope of the general inventive concept.

What is claimed is:

1. A two-photo active compound having a formula:

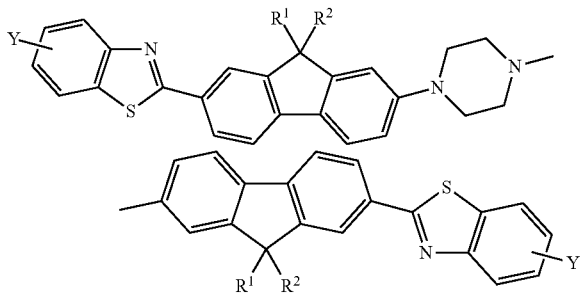

where $R^1$ and $R^2$ are independently selected from the group consisting of linear or branched alkyl chains having a general formula $C_nH_{2n+1}$, n ranges from about 6 to about 20, and ethoxylated alkyls having a general formula $R^3(OCH_2CH_2)_mOCH_2CH_2$—, where $R^3$ is a C1 to C4 alkyl group and m ranges from 0 to about 5; and Y is selected from the group consisting of H, OH, and alkoxyl groups.

2. The two-photon active compound of claim 1, wherein $R^1$ and $R^2$ are independently selected from the group consisting of linear or branched alkyl chains having a general formula $C_nH_{2n+1}$, and wherein n ranges from about 8 to about 18.

3. The two-photon active compound of claim 2, wherein n ranges from about 5 to about 15.

4. The two-photon active compound of claim 1, wherein $R^1$ and $R^2$ are independently selected from ethoxylated alkyls having a general formula $R^3(OCH_2CH_2)_mOCH_2CH_2$—, where R3 is a methyl or ethyl group, and where m ranges from 0 to about 3.

5. The two-photon active compound of claim 4, wherein m is 1.

6. The two-photon active compound of claim 1, wherein Y is $OCH_3$ or $OCH_2CH_3$.

7. The two-photon active compound of claim 1, wherein Y is OH.

8. The two-photon active compound of claim 1, wherein Y is H.

9. The two-photon active polymer of claim 1, wherein $R^1$ and $R^2$ are both ethyl, 3-7-dimethyloctyl, n-decyl, or 2-ethylhexyl and Y is H.

10. A salt complex comprising:
the two-photo active compound of claim 1, and
a Brønsted acid or a Lewis acid comprising a transition metal ion.

11. A method of synthesizing a two-photo active compound having a formula:

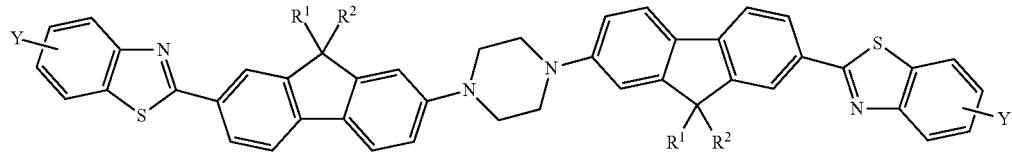

where $R^1$ and $R^2$ are independently selected from the group consisting of linear or branched alkyl chains having a general formula $C_nH_{2n+1}$, n ranges from about 6 to about 20, and ethoxylated alkyls having a general formula $R^3(OCH_2CH_2)_mOH_2CH_2$—, where $R^3$ is a C1 to C4 alkyl group and m ranges from 0 to about 5; and Y is selected from the group consisting of H, OH, and alkoxyl groups, the method comprising:

bis-substituting a 2,7-dihalofluorene compound to form a 9,9-disubstituted-2,7-dihalofluorene compound having a general formula:

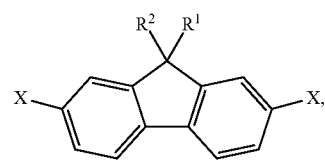

wherein X is I, Br, or Cl.

12. The method of claim 11, further comprising:
mono-formylating the 9,9-disubstituted-2,7-dihalofluorene compound to form a 9,9-disubstituted-2-halo-7-formyl-fluorene compound having a general formula:

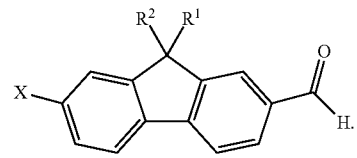

13. The method of claim 12, further comprising:
reacting the 9,9-disubstituted-2-halo-7-formyl-fluorene compound with an ortho-aminothiophenol compound to form a 9,9-disubstituted-2-halo-7-benzothiazole-fluorene compound having a general formula:

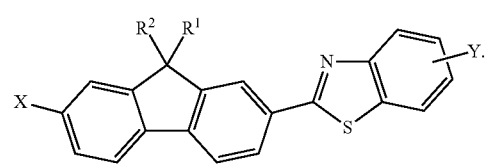

14. The method of claim 13, further comprising:
reacting the 9,9-disubstituted-2-halo-7-benzothiazole-fluorene compound with piperazine to form the two-photo active compound.

* * * * *